US006284546B1

(12) United States Patent
Bryning et al.

(10) Patent No.: US 6,284,546 B1
(45) Date of Patent: Sep. 4, 2001

(54) METHOD AND DEVICE FOR PHOTODETECTION

(75) Inventors: Zbigniew T. Bryning; Benjamin R. Irvin, both of Campbell; Hrair Kirakossian, San Jose; Edwin F. Ullman, Atherton, all of CA (US)

(73) Assignee: Dade Behring Marburg GmbH, Marburg (DE)

( * ) Notice: Subject to any disclaimer, the term of this patent is extended or adjusted under 35 U.S.C. 154(b) by 0 days.

(21) Appl. No.: 08/469,578

(22) Filed: Jun. 6, 1995

Related U.S. Application Data (63) Continuation of application No. 08/260,649, filed on Jun. 16, 1994, now abandoned.

(51) Int. Cl.[7] .................................................. G01N 21/76
(52) U.S. Cl. ........................ 436/172; 250/458.1; 422/66; 422/82.05; 422/99; 436/44; 436/174
(58) Field of Search ..................... 435/7.5, 7.1; 436/533, 436/44, 174, 172, 164; 422/66, 68.1, 82.05, 99; 366/108, 127; 250/458.1

(56) References Cited

U.S. PATENT DOCUMENTS

| Re. 30,627 | 5/1981 | Bagshawe et al. . |
|---|---|---|
| 3,479,141 | 11/1969 | Smythe et al. . |
| 3,526,480 | 9/1970 | Findly et al. . |
| 3,650,698 | 3/1972 | Adler . |
| 3,690,832 | 9/1972 | Plakas . |
| 3,854,703 | 12/1974 | Gibbs et al. . |
| 3,979,181 | 9/1976 | Plakas . |
| 4,065,263 | 12/1977 | Woodbridge, III . |
| 4,121,466 | 10/1978 | Reichler et al. . |
| 4,188,543 | 2/1980 | Brunsting et al. . |
| 4,250,257 | 2/1981 | Lee et al. . |
| 4,349,510 | 9/1982 | Kolehmainen et al. . |
| 4,575,485 | 3/1986 | Sizto et al. . |
| 4,676,656 | 6/1987 | Cook . |
| 4,772,453 | 9/1988 | Lisenbee . |
| 4,988,208 | 1/1991 | Shibuya et al. . |
| 5,082,628 | 1/1992 | Andreotti et al. . |
| 5,201,576 | 4/1993 | Squyres . |

FOREIGN PATENT DOCUMENTS

| 31 15568 A1 | 4/1982 | (DE) . |
|---|---|---|
| 0 272 407 A2 | 6/1988 | (EP) . |
| 0 345 776 A2 | 12/1989 | (EP) . |
| 2163483 | 7/1973 | (FR) . |

OTHER PUBLICATIONS

Smith, et al., Clinical Chemistry, (1982) vol. 28:9, "An Innovative Technology for Random–Access Sampling".

Primary Examiner—Jan Ludlow
(74) Attorney, Agent, or Firm—Theodore J Leitereg; Leland K Jordan; Lois K Ruszala (57) ABSTRACT

The present invention provides methods and apparatus for mixing two or more liquids and detecting light emitted by the mixture. The method comprises forming a liquid droplet containing two or more liquids on a substantially planar surface in containerless containment on the surface and causing the droplet to deform in an essentially zero air flow environment thereby mixing the liquids and surrounding the planar surface with a reflective housing and photodetector. An apparatus of the invention comprises (a) a substantially planar support, (b) means for dispensing liquids onto the support to form a droplet, and (c) non-evaporative means for causing the droplet to deform without deforming the support thereby mixing the liquids and a two part reflective housing and photodetector which is moveable. The drop can be deformed by, for example, application of acoustic energy or a variable electrostatic field. The methods and apparatus have particular application to the determination of an analyte.

7 Claims, 2 Drawing Sheets

METHOD AND DEVICE FOR PHOTODETECTION

This is a continuation of pending application Ser. No. 08/260,649, filed Jun. 16, 1994 now abandoned, the disclosures of which are incorporated herein by reference.

BACKGROUND OF THE INVENTION

1. Field of the Invention

The present invention relates to methods and apparatus for handling small liquid volumes. As used herein and throughout the description and claims directed to this invention, the term "liquid" encompasses liquids alone and liquids containing particulate matter of whatever kind.

The apparatus and method of the present invention have particular application to situations where small liquid volumes are utilized and processed. One such example is the clinical laboratory, in which chemical analyzers are used with liquid samples which are added to reagents and mixed in discrete reaction cups. These reaction-cups are typically molded plastic about the size and shape of a sewing thimble. Sometimes they are of a special shape to include multiple compartments, viewing windows for optics, or shaped for centrifugation. They are usually loaded by hand into some form of automated mechanism although automatic loaders have been built. Complicated mechanisms have been built to move the cups between different locations so that various operations can be performed as required by the analysis method. At the end of the analysis, they must be carefully removed to prevent spilling of materials that may constitute a biohazard. The volumes of the cups are usually quite large, consisting of hundreds of microliters. Mixing of sample and reagents can be done in several ways: employment of centrifugal forces, turbulence due to hydraulic discharge, magnetic stir bars or mixing blades or paddles that require cleaning between successive samples. Discrete plastic cups have moderately thick walls and have poor thermal conductivity, making rapid temperature equilibration difficult even with waterbaths. Additionally, discrete cups can be relatively expensive costing from one to several cents each.

As described more fully below, several approaches have been developed to avoid the use of the above-described containers. One of the more difficult problems encountered in avoiding such containers if providing for adequate mixing when fluids are combined. In one approach small fluid volumes are placed on a deformable support, which can be deformed into a cavity, thus achieving mixing of the liquids contained in the small volume. In another approach liquids are applied in small pools to a support to form a mixture, which is agitated by directing a gas on the liquid.

As will be seen more fully from the description of the invention that follows, the present invention affords a liquid handling system that minimizes, obviates or totally overcomes problems presented by the prior art devices. For example, it is possible to handle very small volumes of liquid, even sample volumes below 50 microliters. The apparatus promotes mixing of the liquid sample within itself or, if mixed with one or more reagents, without using any external mixer that is in contact with the reaction mixture. Additionally, the system yields an apparatus that promotes good thermal conductivity such that temperature gradients throughout the mixed system are minimized. The system additionally exhibits simple and safe disposal of used materials and facilitates lower costs through the use of disposables and reduced labor costs or machine costs due to the absence of discrete reaction cups.

Present day clinical assay instrumentation typically requires numerous disposable components, relatively large amounts of reagents, multiple steps to ensure that all reused components are washed and relatively large amounts of sample. The purpose of the present invention is to minimize reagents and sample use, eliminate buffers, washing solutions, and most of the disposables, decrease the size, complexity and cost of instrumentation, and reduce the volume of waste without interfering with assay performance. All of this is accomplished without evaporation of the liquids or the use of a deformable support.

2. Description of the Related Art

U.S. Pat. No. 3,854,703 (Gibbs, et al.) discloses a method of, and apparatus for, promoting a reaction between a liquid specimen and a liquid reagent. Such reaction is promoted by applying the liquids to a liquid-impermeable support surface to form a mixture thereon. The liquid mixture is agitated by directing a jet of gaseous fluid from a supply duct outlet to impinge thereon, bringing about relative movement between the outlet and the support surface.

A fluid handling system is described in U.S. Pat. No. 4,676,656 (Cook, et al.). A small fluid volume is placed on a reversibly deformable support, which is deformed to form a cavity. As the fluid clings to the surface of the support, it is physically agitated and mixed as the support is deformed. The deformable support can be utilized to provide fluid containers of varying sizes, to accommodate different fluid volumes and as a transport mechanism to move fluid from one location to another.

U.S. Pat. No. 3,479,141 (Smythe, et. al.) discloses a transport system for an automatic analysis apparatus for a series of aqueous liquid samples processed as a flowing stream with no or minimal contamination between samples. A fluorinated hydrocarbon conduit and intersample segments of silicone are employed. The silicone wets and adheres to the fluorinated hydrocarbon conduit, while the aqueous liquid samples do not do so. Where wetting and contacting of the conduit by the samples is required, and in dialysis, glass and/or cellophane are used, which the aqueous liquid samples wet, and the silicone does not.

A metering apparatus is disclosed in U.S. Pat. No. 4,121,466 (Reichler, et. al.). The apparatus is adaptable either as a dispenser or a sampler, the surface of the aspirating probe being coated with a thin film of liquid immiscible with the liquids to be aspirated. The thin immiscible film prevents contamination between segments of successively aspirated liquids and, also, their respective sources. Further, segments of the immiscible liquid can be aspirated between successive liquid segments to maintain such liquid segments discrete.

Smith, et. al., discuss "An innovative technology for 'random-access' sampling" in *clin. Chem.*, 28(9): 1867–1872 (1982). An immiscible, non-reactive fluid is used as a positive barrier between the liquid sample and reagent and the interior and exterior surfaces of their respective probes providing an inert, deformable surface that both prevents carryover and ensures accurate delivery.

U.S. Pat. No. 3,526,480 discusses an automatic chemical analyzer wherein measured portions of sample material are transferred from a sample carrier to discrete reagent-containing sites on an analytical tape. The apparatus is particularly adapted for the transfer of a plurality of different discrete reagent-containing sites. Apertured analytical tapes are disclosed as well as reagent-containing sites that have the reagents chemisorbed therein.

U.S. Pat. No. 4,575,485 (Sizto, et al.) describes ultrasonic enhanced immunoreactions. Rates of binding between members of a specific binding pair, e.g., ligand-receptor, are greatly enhanced by short-term ultrasonication of an aqueous medium containing the specific binding pair. The enhanced rates find particular use in specific binding protein assays.

SUMMARY OF THE INVENTION

One aspect of the present invention is a method of mixing two or more liquids. The method comprises forming a liquid droplet containing two or more liquids on a substantially planar and substantially inelastic surface in containerless containment on the surface and causing the droplet to deform in an essentially zero air flow environment thereby mixing the liquids.

Another aspect of the present invention is a method of mixing two or more liquids wherein a liquid droplet containing the two or more liquids is formed on a substantially planar surface. Electrostatic energy or acoustic energy is applied to the droplet thereby mixing the liquids.

Another method in accordance with the present invention for mixing two or more liquids comprises forming a liquid droplet containing two or more liquids on a substantially planar surface. The droplet is caused to deform in an essentially zero air flow environment without substantially stretching the surface thereby mixing the liquids.

Another aspect of the present invention is an apparatus for mixing two or more liquids. The apparatus comprises (a) a substantially planar support, (b) means for dispensing liquids onto the support to form a droplet, and (c) non-evaporative means for causing the droplet to deform without substantially stretching the support thereby mixing the liquids.

Another apparatus in accordance with the present invention for mixing two or more liquids comprises (a) a substantially planar support, (b) means for dispensing the liquids onto the support to form a droplet, and (c) means for causing the droplet to deform without deforming the support thereby mixing the liquids. The means for causing the droplet to deform is selected from the group consisting of acoustic energy and electrostatic waves.

Another aspect of the present invention is an improvement in a method for transporting liquid samples and reagents through an automatic analysis apparatus. The method comprises forming discrete zones having a liquid sample and reagents on a moving belt, mixing the sample and reagents in the discrete zones to form discrete reaction mixtures and moving the discrete reaction mixtures to a detection zone. The improvement comprises having the discrete reaction mixtures present in the discrete zones in containerless containment in essentially zero air flow during at least the forming and mixing steps.

Another aspect of the present invention is a method for transporting liquid samples and reagents through an automatic analysis apparatus and mixing the sample and reagents during the transport. A substantially inelastic and substantially planar support is moved past one or more pipettes that deliver sample and reagents onto the support to form droplets, each comprising a sample and reagents. The droplets are deformed in an essentially zero air flow environment, thereby mixing the sample and said reagents.

Another method in accordance with the present invention is concerned with transporting liquid samples and reagents through an automatic analysis apparatus and mixing the sample and reagents during transport. A substantially inelastic and substantially planar support is moved past one or more probes that deliver sample and reagents onto the support to form droplets, each comprising a sample and reagents. Electrostatic energy or acoustic energy is applied to the droplets thereby mixing the sample and the reagents.

An automatic analysis apparatus in accordance with the present invention for analyzing a plurality of samples comprises (a) a movable substantially planar first support, (b) a rigid second support for the first support, (c) one or more liquid dispensing pipettes for dispensing a sample and reagents onto the first support to form droplets, each containing a sample and reagents, (d) non-evaporative means for deforming the droplets without substantially stretching the first support thereby mixing the sample and the reagents contained in the droplets, and (e) means for analyzing the droplets.

Another aspect of the present invention is a method for assaying for the presence or amount of an analyte in a sample suspected of containing the analyte. The method comprises moving a substantially planar surface past one or more probes that deliver sample and reagents onto the surface to form droplets. Each droplet comprises a sample and reagents wherein one of the reagents is a labeled reagent or a reagent capable of being labeled. Electrostatic energy or acoustic energy is applied to the droplets thereby mixing the sample and the reagents. Next, the droplets are incubated on the surface and the amount of signal generated by the labeled reagent is determined without removing the droplet from the surface. The amount of such signal is related to the presence of amount of said analyte in said sample.

Another aspect of the present invention is a method for detecting light emitted from a liquid medium subjected to photoactivation. The method comprises (a) applying the medium to a transparent support and (b) positioning the support such that the medium and the support are between two reflective surfaces that substantially surround the medium. At least one of the surfaces has an opening for light emitted from the medium to impinge on a photodetector.

Another aspect of the present invention is a device for detecting light emitted from a liquid medium subjected to photoactivation. The device comprises a transparent support, a photodetector and two reflective surfaces. The surfaces are positioned with respect to the support such that a medium applied to the support lies between the surfaces, which substantially surround the medium. At least one of the surfaces has an opening for light emitted from the medium to impinge on the photodetector.

DESCRIPTION OF THE SPECIFIC EMBODIMENTS

The present invention provides for efficient mixing of very small volumes of liquid such as, for example, 50 microliters or less. The invention has particular application in automatic analysis apparatus such those used to conduct automated assays. In this aspect the invention provides for random access to liquid samples and reagents for carrying out such assays and for transporting such samples and reagents through the apparatus while at the same time mixing the samples and reagents and providing for detection of a signal. All of the above are accomplished using non-evaporative techniques and without the need of a container or a deformable support. The benefits of the present invention are achieved by forming a liquid droplet containing two or more liquids on a substantially planar surface and causing the droplet to deform in an essentially zero air flow environment without deforming the surface. Particularly preferred approaches for deforming the droplet are application to the droplet of electrostatic energy or acoustic energy. The present invention permits one to minimize reagents and sample use, eliminate buffers, washing solutions, and most of the disposables, decrease the size, complexity and cost of instrumentation, and reduce the volume of waste without interfering with assay performance.

Figure 1:
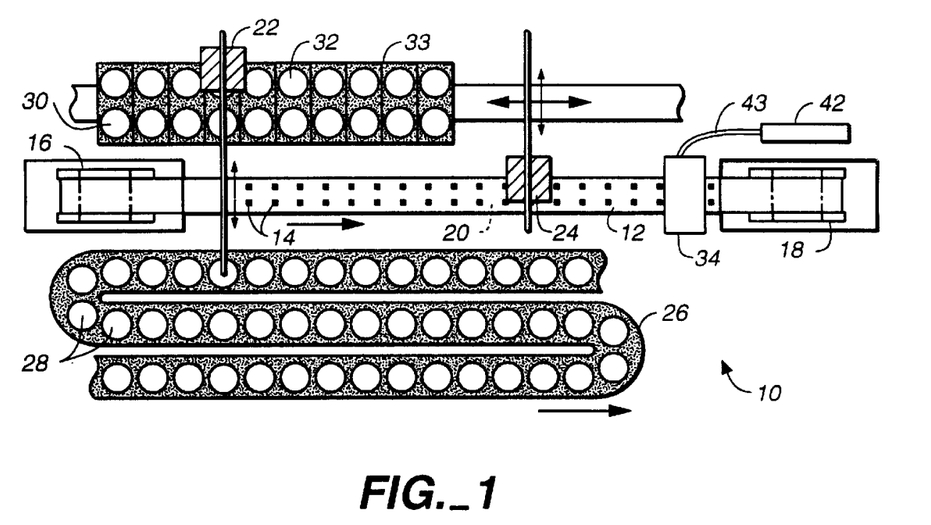
FIG. 1 is a top view of an embodiment of the present invention.
Figure 2:
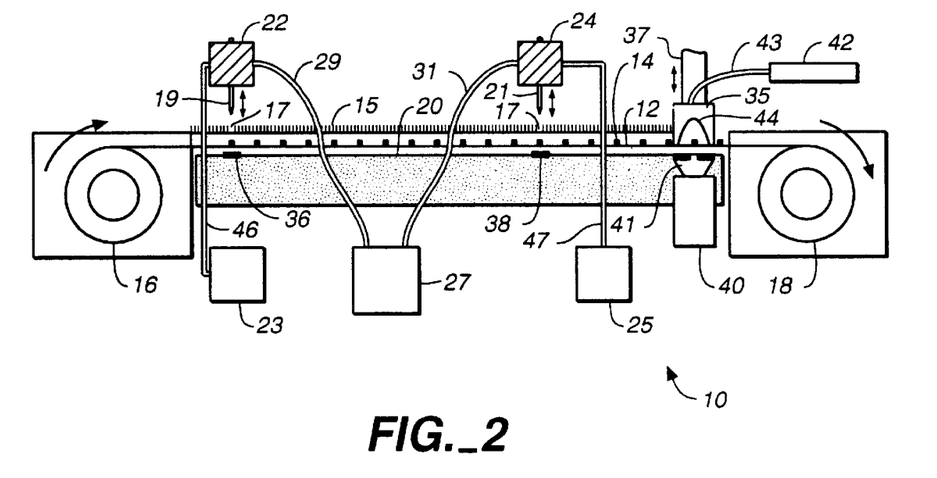
FIG. 2 is a side view of the embodiment of FIG. 1 absent the serpentine belt containing the sample cuvettes.

Specific embodiments of the present invention are next described in detail with reference to the attached drawings by way of illustration and not limitation. A particular embodiment of the invention is illustrated in FIG. 1 and FIG. 2. Fluid handling apparatus 10 comprises a first support 12 for depositing droplets of liquid 14 thereon. Support 12 is substantially planar and generally impervious to the deposited liquids. The term "substantially planar" means that the plane of surface 12 is such that liquid droplets placed thereon will not be caused to move by gravity to any substantial degree from the point of deposit. In the embodiment the liquid droplets preferably remain at the point of deposit.

Furthermore, support 12 is substantially free of binding members, i.e., a member of a specific binding pair that has an area on the surface or in a cavity that specifically binds to, and is thereby defined as complementary with, a particular spatial and polar organization of the other member of the pair. The members of-the specific binding pair are referred to as ligand and receptor (antiligand). These may be members of an immunological pair such as antigen-antibody, or may be members of such pairs as operator-repressor, nuclease-nucleotide, biotin-avidin, hormones-hormone receptors, nucleic acid duplexes, IgG-protein A, and the like.

Support 12 is manufactured from a material that is relatively inelastic and substantially impervious to and non-reactive with deposited liquids. The support is constructed such that it is not readily stretched or deformed to an extent greater than required to be rolled onto a spool in an embodiment where the support is housed in a cassette. Furthermore, surface 12 does not provide for any specific chemical interaction, such as antigen-antibody interactions, of such surface with the components of the liquid sample or liquid reagents and may or may not be wet by the liquids. Suitable materials for support 12 are, by way of illustration and not limitation, polystyrene, polyurethane, nylon, polyesters, polymethacrylate, polyethylene, polypropylene, polyfluorocarbons, nitrocellulose, cellulose acetate, etc. The material is preferably transparent and colorless or it may be opaque whereupon it is usually black or white. For certain methods it is desirable to use a support that is coated, for example, metalized on one or both sides. Such coating may be used to control reflectivity, electrostatic phenomena, etc., or patterns can be provided that result in electrical contacts with the sample that permit an electrolytic process or a photoacoustic measurement or production of diffraction patterns.

The thickness of support 12 is usually about 0.002 to 0.04 inches, preferably, 0.004–0.020 inches. The particular thickness employed will depend on the strength of the material chosen and may also depend on the ability of the material to conduct heat and electrostatic or acoustic energy. It is evident that the thickness of the support should be such as to permit the support to retain its integrity during use in the present invention. The width of the support is generally determined by the particular application in which the invention is used such as in an automated analysis apparatus. In the latter situation the support can be provided as a fiber, flexible strip, sheet or tape that may be wound into a roll or provided as a cassette for ease in dispensing. In this approach support 12 can be taken up by a roll at the exit of the apparatus. The width of the strip in such circumstance is 0.004 to 10 inches, preferably, 0.4 to 5 inches. In general, it is preferable that the thickness and width of the strip be relatively uniform.

It may be important in some circumstances to ensure that support 12 is substantially free of electrostatic charge. To this end the surface may be coated with ionic detergents or metalized or the charge can be controlled through grounding, wiping with a conductive material or subjecting to alpha particle irradiation.

In FIG. 1 support 12 is in the form of a flexible strip that is in cassette 16 and is taken up by cassette 18. The strip provides for transport through apparatus 10. Conventional mechanisms for driving the strips can be employed such as the use of gears and perforations in the strip, friction drives, rotation of the uptake reel in the cassette, and so forth. Additionally, control of such drive mechanisms using microprocessor units and techniques can be conveniently applied to provide automated systems. In this way smooth movement of the support through the apparatus is maintained. This particular embodiment allows for all of the liquid on the surface of the support, as well as the used portions of the support, to be taken up in the cassette in a safe manner for eventual disposal. It should be evident that in the above embodiment the only disposable item is the cassette containing the used support and liquids. There is no need for special wash solutions to clean any of the components of the present device. Any sample or reagents that might adhere to the pipette are expelled using a minute amount of immiscible liquid and, as mentioned above, all liquids are taken up in the cassette. Of course, it is within the scope of the present invention to move support 12 through a disposal station to remove the liquid from the support by suction or otherwise. If desired, that portion of the support that has been used can then be cut off and disposed of in an appropriate container for safe disposal.

For simplicity only one support is shown in FIG. 1; it should be understood that a plurality of supports may be present in one analytical apparatus in accordance with the present invention. Support 12 is optionally supported by rigid support 20 (shown in phantom in FIG. 1 and full view in FIG. 2), which may be made from any material that provides for rigidity such as rigid plastic, metal, ceramic, and the like. Rigid support 20 may be the same width as support 12 or it may be wider or narrower than support 12, usually no more than 50% larger or smaller. Alternatively, rigid support 20 is provided with rolled edges, beads, ribs or thickened sections to provide rigidity to support 12 when support 12 is not made of a rigid material. It must be kept in mind that the rigidity of support 12, either by itself or through the use of a rigid support 20, must accommodate the type of feeding mechanism. Cover 15 may be used to protect support 12 and its contents during use. Openings 17 permit access of pipettes 22 and 24 to support 12. Cover 15 may be made of any suitable material consistent with its use such as plastic, metal such as aluminum, and so forth.

It is also within the purview of the present invention that support 12 not be movable, although this is less preferred.

The various devices that must interact with the support are then movable. Alternatively, support 12 may be a disposable disk or plate that may be mounted on a transport system such as a carousel. In another embodiment support 12 may be a discrete plate large enough to accommodate fluid drops for a few, e.g., one to three, assays. In one aspect of this latter embodiment the support plate is inserted into a transport mechanism associated with rigid support 20 and includes an integral container for a single sample in place of cuvettes 28.

Apparatus 10 further comprises liquid dispensing means such as pipettes 22 and 24 for dispensing liquid sample and reagents onto the surface of support 12 in the form of droplets 14. Pumps 23 and 25, which may be, for example, peristaltic proportioning pumps or syringes, cooperate by means of conduits 46 and 47 with pipettes 22 and 24, respectively, to allow for aspiration and dispensing of liquid onto support 12. Examples of other pumps that may be used in the present invention are capillary, piezoelectric, compression, and the like. The total volume of liquid in droplets 14 from the sample and the reagents is usually about 1 to 100 microliters, preferably, less than 50 microliters, usually about 15 to 40 microliters. The pipettes, including their tips, are usually nondisposable. Such pipettes are conventional in the art. Pipette 22 communicates with liquid sample dispensers or cuvettes 28, containing samples to be tested, which are transported past pipette 22 on moving serpentine belt 26. The movement of belt 26 is indexed to present each sample at a predetermined interval. The indexing of the moving belt is coordinated with the indexing of support 12, which may be indexed at a predetermined speed so as to permit appropriate periods of incubation based on a particular protocol for an assay. The various parts of apparatus 10 may be indexed, individually or jointly, such that liquid dispensing is responsive to the position of support 12 as indicated by the indexing means. For example, for typical assays the movement of support 12 may be indexed at a rate of 1 to 10 times per minute.

Pipettes 22 and 24 are moved horizontally and vertically by actuator arms (not shown) in accordance with well-known practice.

Apparatus 10 also has reagent cassettes 30 and 32 that contain liquid reagents for conducting an assay. Normally, the liquid reagents are prediluted to a certain predetermined concentration. Cassettes 30 and 32 are on platform 33, which oscillates back and forth so that pipettes 22 and 24 may communicate with cassettes 30 and 32 to add liquid reagents to droplets 14. The movement of platform 33 is indexed so that it is coordinated with the movement of support 12 ensuring that the assays proceed in a desired manner.

Pipettes 22 and 24 are usually treated such that the inside and outside of the inlet ends or tips 19 and 21, respectively, of such pipettes is maintained wet with a liquid that is immiscible with the liquid to be dispensed. The immiscible liquid is contained in reservoir 27. Communication between pipettes 22 and 24 with reservoir 27 is accomplished by way of conduits 29 and 31, respectively.

One such way of maintaining pipettes wet with the immiscible liquid is discussed by Reichier (supra) In this regard a thin film of liquid that is characterized as being immiscible with the liquids to be dispensed is provided over the peripheral and internal surfaces of pipettes 22 and 24. The thin film usually is about 0.00004 to 0.04 inch thick, preferably, 0.0004 to 0.004 inch thick. The thin film preferably wets the internal and peripheral pipette surfaces to the exclusion of the liquids to be dispensed. In order to achieve this effect the immiscible liquid can be flowed past the internal surface where the peripheral surface can be wet by surface attraction or flowed over the peripheral surfaces and the runoff can be aspirated by the pipette or the pipette can be immersed into a reservoir of such immiscible liquid. The immiscible liquid may be supplied to the tip of a pipette from a port other than that through which the sample and/or reagents are supplied to the pipette. However, the immiscible liquid may be supplied through the same port. The specific density of the immiscible liquid may be greater or less than that of the liquids to be dispensed.

The nature of the immiscible liquid is dependent on the material that forms the surfaces of pipettes 22 and 24. The liquid must be able to wet the material, which will usually be relatively hydrophobic, that is, it will preferably be more readily wet by the liquid than by the normally aqueous samples. Immiscible liquids may include silicon oils, mineral or vegetable oils, fluorocarbon oils, etc., the primary requirement being that they be relatively insoluble in water and have low volatility below 50 C. Since it is preferable that components of the test solution have low affinity for the oil, fluorocarbon and silicon oils are usually preferred. Preferably, the immiscible liquid has a viscosity of 0.1–500 centistokes, preferably, 1–100 centistokes, where the viscosity used will depend on the particular immiscible liquid, e.g., a lower viscosity fluorocarbon may be used relative to the viscosity of silicone oil. Immiscible liquids having a viscosity on the low end of the above range may require more cleaning of the tips than those on the higher and of the above range. Further details on this subject can be found in U.S. Pat. No. 4,121,466 (Reichler), the disclosure of which is incorporated herein by reference in its entirety. In no case must there be any chemical interaction of the immiscible liquid on the pipette tip with the liquid sample or the liquid reagents. Droplets 14 usually contain not only liquid sample and liquid reagents but also some immiscible liquid.

Droplets 14 are on the surface of support 12 in containerless containment. The term "containerless containment" means that droplets 14 are not enclosed in discrete containers having walls or physical barriers that confine the liquid. Droplets 14 are primarily held on the surface of support 12 by means other than gravity such as electrostatic interactions and surface tension. The area adjacent the sites of delivery of liquids will preferably have no mechanical barrier that contacts the droplet. Where such a barrier is used, its principal function is to prevent the droplet from sliding along the surface. For this purpose the surface is provided with shallow depressions or slightly raised elements, and, therefore, the droplets are in contact with the surface to less than 50% of their height, normally, less than 10% of their height. It is within the scope of the present invention to use a surface that has a different affinity for the liquids than the portion of the surface upon which droplets 14 are applied to assist in maintaining the droplets as discrete entities. Another means would be the application of a ring of material (very thin layer) that prevents wetting by oil or water, thus forcing the drops to stay where they are placed.

The method for mixing in accordance with the presence invention employs the interplay of an externally imposed deforming force and the restoring cohesive forces (surface tension) of the drop. The external force is pulsed so that a rapid, oscillating deformation of the drop occurs. Many modes of oscillating deformation are possible and are distinguished by the patterns of relative motion of the various regions of the surface of the drop. The frequency, waveform, and amplitude of the pulsed external force, together with the surface and bulk properties of the drop, determine the mode of oscillating deformation. Rapid and efficient mixing requires the proper choice of these external force control parameters.

The external force may be electrostatic or mechanical. A pulsed electrostatic force or oscillating electric field may be applied by alternately charging and discharging electrodes arrayed in the vicinity of the droplet. A pulsed mechanical force may be applied by displacing the support tape with an actuator driven by a voice coil, piezoelectric membrane, or other oscillatory electromechanical transducer.

The liquid sample and the liquid reagents are mixed in an essentially zero air flow environment to avoid evaporation and movement of the droplets other than that consistent with the present invention. By the term "essentially zero air flow environment" is meant that the movement of air in device 10 in the area in which the liquids are to be mixed is insufficient to cause movement or deformation of liquid droplets 14. Further, to avoid evaporation surface 12 is usually enclosed to provide a minimum air space above the droplets while still providing access to apply sample and reagents.

Device 10 also comprises means 36 and 38 for mixing of the liquid sample and the liquid reagents in droplets 14 in accordance with the present invention. Generally, the liquids are mixed by deforming droplets 14 and this is accomplished usually without any substantial stretching of support 12. Accordingly, although support 12 may be thin and, in some circumstances, flexible, support 12 should remain substantially undeformed such that the dimensions of any segment of support 12 remains substantially unchanged, usually, less than 10%, preferably, less than 1% change, in any dimension during mixing of the sample.

Exemplary of means 36 are means for applying electrostatic energy or acoustic energy to droplets 14. Electrostatic energy may be applied by subjecting droplets 14 to a variable electric field, which induces polarization of, and results in deformation of, droplets 14. The variable electric field can be produced by alternately changing the polarity of a capacitor. The deformation of droplets 14 results in mixing of the liquid sample and liquid reagents. No physical contact with droplets 14 is required. The frequency and the field strength of the electric field is dependent on the size, viscosity and surface tension of the drop, the amount of the immiscible liquid in contact with the drop, the characteristics of surface 12, and the like, and is usually determined empirically. Normally, the frequency of the electric field is about 5 to 50,000 Hz, preferably 15 to 1000 Hz, more preferably, about 20 to 500 Hz. The field strength of the electric field is usually about 500 to 20,000 volts per centimeter, preferably, about 1000–10,000 volts per centimeter. The time of application of the electric field energy may vary, depending on the frequency and field strength, from about 1 to 60 seconds, preferably, from about 5 to 20 seconds. The frequency, field strength and time are chosen so as not to have a deleterious effect on the sample, reagents or the accuracy of an assay.

When acoustic energy is applied to the droplets to mix the liquids, the factors enumerated above with respect to the use of an electric field are also applicable. Normally, the vibration necessary for mixing can be achieved by the use of sonic or subsonic energy. To this end droplets 14 can be subjected to a frequency of about 20–20,000 Hz, preferably, 20–2000 Hz. The power is generally dependent on several factors including how the power is coupled to the droplet and the support. Accordingly, the power will be determined for each particular application using the above parameters and guidelines. The time of application of acoustic energy may vary, depending on the frequency and power, from about 0.5 to 30 seconds, preferably, from about 1 to 10 seconds. The power, frequency and time are chosen so as not to have a deleterious effect on the sample, reagents or the accuracy of an assay. Acoustic energy is applied to droplets 14 in apparatus 10 by means of an acoustic wave generator, loudspeaker, or the like.

Another method for mixing the liquids in droplets 14 involves shear forces produced by drawing each droplet into and out of the tip of a pipette such as pipette 22 or through a mixing device within the tip of such pipette. This may be achieved by the use of pulp 23 cooperating with the pipette and operated in an intermittent fashion.

Apparatus 10 also includes means for measuring a signal produced in droplet 14 during the course of an assay. Such means for measuring a signal, or analyzer, is dependent on the type of signal produced in the assay, which is described in more detail below. Briefly, the signal usually is or is produced by electromagnetic radiation and results from light absorbance and scattering, fluorescence, chemiluminescence, resonance Raman, photoacoustic spectroscopy, electroluminescence, magnetization, and the like. One such means for measuring a signal is read head 34 positioned in apparatus 10 so that read head 34 can examine droplets 26 for the presence of a signal. Read head 34 may comprise a light source, photodetector, acoustic wave detector, a magnetometer, a means for causing electrolysis of the sample and a photodetector, a scintillation counter, or the like.

In FIGS. 1 and 2 read head 34 comprises an upper portion or parabolic reflector 35 that sits directly over a portion of support 12 and comprises reflective surface 44. A laser 42 communicates with upper portion 35 by means of optical fiber 43. Read head 34 also comprises photomultiplier tube 40 having shutter 41. The movement of upper portion 35 vertically to and from support 12 is controlled by arm 37 which in turn is controlled by, for example, a solenoid (not shown).

Preferably, the signal is read without further contacting of droplets 14. However, measurement of the signal may be achieved by drawing a portion of droplet 14 into a reading chamber that is coated with an immiscible liquid such as described above. Where the signal is light, an appropriate lens or light pipe system may be included to collect the light emitted from a droplet with high efficiency.

The samples will frequently be, but are not limited to, samples of biological origin and include body fluids, usually obtained from the body of a mammalian subject. The body fluids are generally liquid or semi-solid material and may be sterile or nonsterile and may contain cells. The body fluid may be employed without further treatment or it may be treated to remove cells, debris, and the like Exemplary body fluids are whole blood, lymphatic fluid, serum, plasma, saliva, semen, and cerebral spinal fluid. Body fluid may be removed from a subject, for example, by means of a syringe or needle or by natural expulsion. Other liquid samples may be obtained from semi-solid or solid material by extraction according to known procedures.

Samples to be analyzed by the method of the present invention may be pretreated to separate or lyse cells; precipitate, hydrolyse or denature proteins; hydrolyze lipids; solubilize analyte; or the like. Such pretreatment may include, without limitation, centrifugation; treatment of the sample with an organic solvent, for example, an alcohol, preferably an alcohol having less than about 7 carbon atoms such as methanol; and treatment with detergents, chaotropic agents, sodium hydroxide, etc. Accordingly, the term "liquid sample" includes the above together with any liquid medium produced as the result of such pretreatment and suspected of containing an analyte or component of interest. Such analytes or components of interest include drugs of abuse, therapeutic drugs, pesticides, proteins, such as immunoglobulins, nucleic acids, and so forth. The analytes are described in more detail in U.S. Pat. No. 5,248,619 at column 6, line 27, to column 8, line 6, the disclosure of which is incorporated herein by reference.

The reagents in cuvettes 30 and 32 are selected based on the type of assay to be conducted. The depiction of only two reagents is by way of example only and is not meant to be a limitation. The number of reagents can be more or less depending on the particular assay format utilized. The devices of the present invention may be adapted to most assays that require electromagnetic radiation for detection including assays involving specific-binding pair (sbp) members. The assays may be competitive or sandwich, but will not require separations to be carried out in apparatus 10. The immunological reaction for a sandwich type assay usually involves an sbp member that is bound to a label and the sample. In a competitive protocol the label may be associated with an sbp member that is analogous to the analyte to be determined in the sample. The reagent containing the label, e.g., sbp member linked to a label, is referred to as the labeled reagent. The label may not be bound to an sbp member that is complementary to an analyte. Rather, the reagent may have an sbp member that will permit the label to become bound to the sbp member bound to an analyte and, thus, is capable of being labeled.

Various ancillary materials will frequently be employed in an assay employing the present invention. Accordingly, the liquid reagents may include buffers as well as stabilizers for the assay medium and the assay components and for wash steps as required. Frequently, in addition to these additives, additional proteins may be included, such as albumins, or surfactants, particularly non-ionic surfactants, binding enhancers, e.g., polyalkylene glycols, or the like.

After the sample and reagents have been combined, they can be incubated, if desired. The sbp members are then activated and the resulting signal is measured. For example, if the sbp members are an enzyme label and its substrate, substrate is added and the signal produced is related to the amount of analyte in the sample tested.

For a more detailed discussion of immunoassay techniques to which the present invention may be applied, see "Enzyme-Immunoassay," by Edward T. Maggio, CRC Press, Inc., Boca Raton, Fla., 1980. See also, for example, U.S. Pat. Nos. 3,690,834; 3,791,932; 3,817,837; 3,850,578; 3,853,987; 3,867,517; 3,901,654; 3,935,074; 3,984,533; 3,996,345; and 4,098,876, which listing is not intended to be exhaustive.

The signal from the label may be directly detectable such as a radiolabel. On the other hand the label may be part of a signal producing system ("sps"), which may have one or more components, at least one component being the label. The sps generates a detectable signal that relates to the amount of bound and/or unbound label, i.e. the amount of label bound or not bound to the analyte being detected or to an antibody against such analyte. In this way the amount of signal is related to the presence or amount of analyte in the sample. Calibrators or controls containing predetermined amounts of analyte can be employed to assist in relating the amount of signal to the presence or amount of analyte. The "sps" includes all the reagents required to produce a detectable signal. There are numerous methods by which the label can produce a detectable signal, for example, by electromagnetic radiation, heat, chemical reagents, and the like.

The label can directly produce a signal, i.e., additional reagents are not required to produce a signal. For example, numerous organic molecules are able to absorb ultraviolet and visible light, where the light absorption transfers energy to these molecules and elevates them to an excited energy state. This absorbed energy is then dissipated by emission of light at a second wavelength. For example, fluorescent molecules are able to absorb light at one wavelength and emit light at a second wavelength. Suitable fluorescent molecules include fluorescein, isothiocyanate, rhodamine, phycoerythrin, phycocyanin, allophycocyanin, o-phthaldehyde, and fluorescamine. A large number of illustrative fluorescers are indicated in Litman, et al., U.S. Pat. No. 4,275,149, columns 30 and 31, which disclosure is incorporated herein by reference. Other examples of labels that can directly produce a signal are radioactive isotopes, such as $^{125}I$, $^{131}I$, $^{14}C$, $^{3}H$, $^{57}Co$, $^{75}Se$, $^{32}P$, $^{35}S$, and the like; and dyes, such as are well known in the art.

Alternately, the label may also require other reagents in order to produce a signal. Therefore, the signal producing system includes all of the reagents required to produce a measurable signal. Other components of the signal producing system include substrates, coenzymes, enhancers, second enzymes, activators, cofactors, inhibitors, scavengers, metal ions, specific binding substance required for binding of signal generating substances, and the like. Some of the chemical reagents such as coenzymes, substances that react with enzymic products, other enzymes and catalysts, and the like can be bound to other molecules or to a support.

A wide variety of non-enzymatic catalysts that may be employed are found in Ullman, U.S. Pat. No. 4,160,645, the appropriate portions of which are incorporated herein by reference.

An enzyme or coenzyme may be employed that provides the desired amplification by producing a product, which absorbs light, e.g., a dye, or emits light upon irradiation, e.g., a fluorescer. Alternatively, the catalytic reaction can lead to direct light emission, e.g., chemiluminescence. A large number of enzymes and coenzymes for providing such products are indicated in Litman, et al., U.S. Pat. No. 4,275,149 bridging columns 19 to 23, and Boguslaski, at al., U.S. Pat. No. 4,318,980, columns 10 to 14, which disclosures are incorporated herein by reference.

Chemiluminescent compounds are also suitable as labels such as, by means of illustration and not limitation, luminol, isoluminol, aromatic acridinium esters, imidazole, acridinium salt, oxalate ester, and the like. Numerous chemiluminescers are set forth in Litman, et al., U.S Pat. No. 4,275,149, column 31, which disclosure is incorporated herein by reference. Chemiluminescers can also be used in conjunction with photosensitizers, such as is described in U.S. Ser. No. 07/704,569, filed May 22, 1991 entitled "Assay Method Utilizing Induced Luminescence", which disclosure is incorporated herein by reference.

One particular method for generating a signal in assays conducted in accordance with the present invention is described in U.S. patent application Ser. No. 07/704,569 filed May 22, 1991 (Ullman, et al.), the relevant disclosure of which is incorporated herein by reference. The method comprises treating a reaction mixture suspected of containing the analyte under conditions such that the analyte, if present, causes a photosensitizer and a chemiluminescent compound to come into close proximity. The photosensitizer generates singlet oxygen and activates the chemiluminescent compound when it is in close proximity. The activated chemiluminescent compound subsequently produces light. The amount of light produced is related to the amount of analyte in the medium. More particularly, as applied to the present invention, one embodiment of the method comprises as a first step providing a combination comprising the aforementioned medium suspected of containing analyte bound to a particle which also has a chemiluminescent compound associated with the particle, a photosensitizer associated with a specific binding pair (sbp) member capable of binding to the analyte. The combination is treated, usually by irradiation with light, to excite the photosensitizer, which is capable in its excited state of activating oxygen to a singlet state. The combination is then examined for the amount of luminescence or light emitted. The amount of such luminescence is related to the amount of analyte in the medium. Alternatively, the chemiluminescent compound is associated with an sbp member capable of binding the analyte, and the particle to which the analyte is bound is associated with a photosensitizer.

After appropriate incubations droplets 14 pass through read head 34, where the signal generated is determined.

The apparatus of the present invention can be enclosed in a case to protect it during use and storage. Such cases are well-known in the art and may be of any design consistent with the function and use of the present apparatus. In addition, the working parts of the apparatus are generally controlled by various software to provide for the necessary functions such as indexing of support 12, aspiration and dispensing of liquids, coordination of other parts of apparatus 10, and the like. The present apparatus can include means for controlling the interior temperature so that appropriate incubation temperatures and the like are obtained. Such means can include various heating and cooling mechanisms, which are conventional in the art.

In a preferred protocol for assays conducted in accordance with the present invention and employing a total liquid volume of less than 50 microliters, the tip of pipette 22 is first wet by forcing a few microliters of an immiscible liquid through the tip. The immiscible liquid is held in reservoir 27 and delivered to pipette 22 by means of a valve in conduit 29. Any excess immiscible liquid can be delivered to the surface of support 12. Next, the immiscible liquid is replenished to wet the tip of the pipette and several microliters of a liquid reagent from cuvette 32 are drawn up followed, if desired, by aspiration of a few microliters of a liquid sample from cuvette 28 or a second liquid reagent from cuvette 32. Usually, when a second reagent or the sample is aspirated, a small air gap is introduced between the two liquids by aspiration of a small amount of air. The two liquids are than delivered onto the surface of support 12. Alternately, the smaller volume of liquid to be used is delivered directly onto the surface and the second liquid is subsequently aspirated and delivered on top of the drop of the first liquid. Generally, the tips of pipettes 22 and 24 are wet with the immiscible liquid prior to each aspiration and dispensing of liquid by taking up the immiscible liquid from reservoir 27. The drops may be placed on support 12 at any location as long as the edges of the support do not interfere with the containerless containment of the drops either before, during and after mixing of the liquids in accordance with the invention. It may sometimes be preferred to locate drops on the support so as to maximize the consistency of the results of an assay and to avoid anomalous results.

Next, an electric field is actuated to mix the liquids in droplet 14. Following the mixing of the liquids, the assay mixture is allowed to incubate for 0.5 to 30 minutes. Other liquid reagents may be added during this time or an aliquot of the mixture can be drawn up by a pipette tip and delivered to another portion of the surface. Another reagent can then be delivered on top of this new droplet and the combination again mixed as described above. During this entire time support 12 is stepwise moving from one end adjacent cassette 16 to the other end adjacent cassette 18. All of the above steps are indexed in an appropriate manner. Following all of the mixing and incubation steps, a signal produced during the assay as a result of the presence or absence of an analyte in the liquid sample is read by read head 34. For example, where the signal is electromagnetic radiation such as with a fluorescent or chemiluminescent label, generally, the assay mixture is irradiated and the amount of light emitted is measured. For this purpose it will sometimes be useful for the surface of the support to have a reflective coating to assist in light collection. Such reflective coating can be, for example, commercially available aluminized Mylar.

Support 12 continues to move so that it is taken up into cassette 18 for disposal. As mentioned above, it is within the scope of the present invention to use a support that can be cut off, retained or dispensed in a safe manner. While separate liquid sample dispensing means, reagent dispensing means and liquid removal means have been described, those functions can be variously combined in conventional ways depending on the particular application. For example, a single pipetting mechanism could be utilized for dispense liquid sample and reagents as necessary and also to remove liquid from support 12 at the end of an assay if desired. Various modifications of this illustrative system will be apparent for particular applications and instrumentation, which can include a variety of substance detection systems for the detection and/or measurement of materials in liquids.

Figure 3:
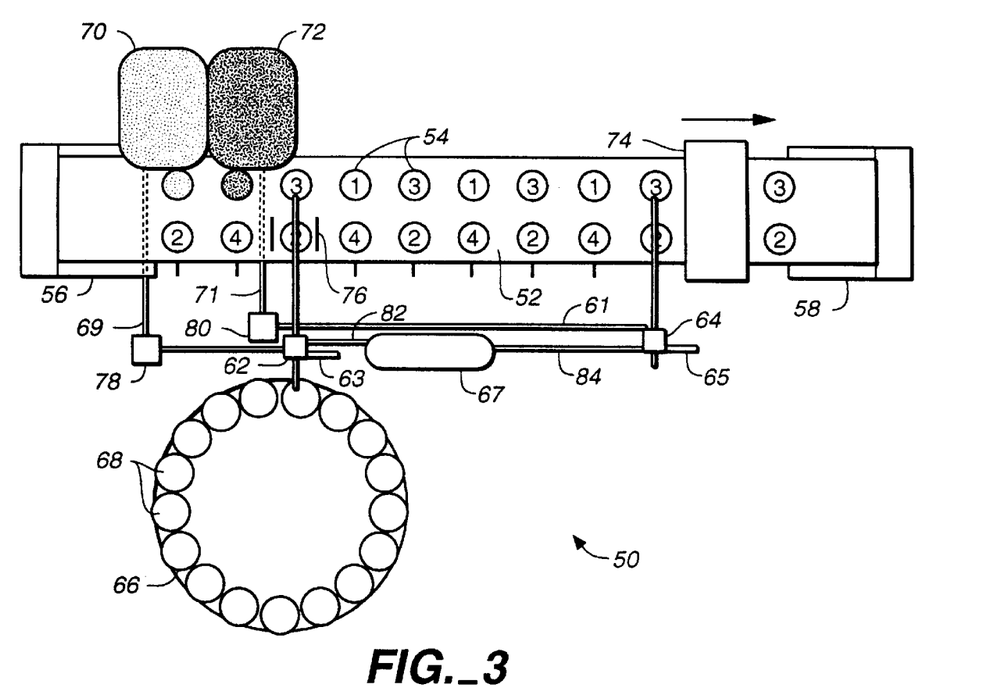
FIG. 3 is a top view of another embodiment of the present invention.

Another device in accordance with the present invention is shown in FIG. 3. Apparatus 50 comprises a support 52 for depositing droplets of liquid 54 thereon. Support 52 is substantially planar and generally impervious to the deposited liquids. In FIG. 3 support 52 is in the form of a flexible strip that is in cassette 56 and is taken up by cassette 58, which provides for transport through the apparatus. Apparatus 50 further comprises liquid dispensing means such as pipettes 62 and 64 for dispensing liquid sample and reagents onto the surface of support 52 in the form of droplets 54. As with the apparatus described in FIG. 1, it is desirable to maintain the tips of pipettes 62 and 64 wet with a liquid that is immiscible with the liquid to be dispensed. Pipettes 62 and 64 communicate with reservoir 67 by means of conduits 82 and 84 and assisted by pumps 63 and 65. Reservoir 67 contains a liquid that is immiscible with the liquid to be dispensed. Pipette 62 communicates with cuvettes 68, containing samples to be tested, which are transported past pipette 62. Cuvettes 68 are carried on carousel 66, which may be intermittently rotated, or indexed, to present each sample at a predetermined interval. The indexing of carousel 66 is coordinated with the indexing of support 52, which may be indexed as described above for FIG. 1. Apparatus 50 also has disposable reagent containers 70 and 72 that contain reagents for conducting an assay. Pipette 62 communicates with container 70 by means of conduit 69 and pump 78. Pipette 64 communicates with reagent container 72 by means of conduit 71 and pump 80. The communication is indexed to coordinate with the indexing of the movement of support 52.

The numbers 1–4 within droplets 54 in FIG. 3 identify droplets containing reagent 1 (drop number 1), reagent 2

(drop number 3), sample and reagent, (drop number 2) and combination of reagents 1 and 2 with sample (drop number 4). In FIG. 3 pipettes 62 and 64 not only dispense sample and reagents as droplets 54 as mentioned above, but they also take precise aliquots of each of drops 1–3 and dispense those aliquots to form drop number 4. Alternatively, pipettes 62 and 64 can dispense precise aliquots of reagents and sample directly to form drop number 4 (embodiment not shown). In a typical apparatus in accordance with the present invention, containers 70 and 72 are but two of a plurality of such containers, which plurality is in the form of, for example, a wheel, a reciprocating plate, or the like to provide all of the reagents necessary to conduct assays for a multitude of analytes.

It is, of course, within the purview of the present invention to have containers 70 and 72 directly deposit reagents on support 52 as drops number 1 and 3, respectively. In this approach each of containers 70 and 72 is equipped with pipetting means to dispense its respective contents as drops on support 52.

Apparatus 50 also comprises means 76 for mixing of the liquid sample and the liquid reagents in droplets 54 (drops number 4) in accordance with the present invention. In this embodiment means 76 is an acoustic wave generator, for application of acoustic energy to droplets 54. Read head 74 is positioned in apparatus 50 so that read head 74 can examine droplets 54 (drops number 4) for the presence of a signal.

EXAMPLES

The invention is further demonstrated by the following illustrative example, which should not be construed as a limitation on the scope of the present invention. Parts and percentages are by weight unless otherwise indicated.

Example 1

Digoxin Assay

In the present example the method is a homogeneous immunoassay of human blood serum for the presence of the drug digoxin. The method that was automated in accordance with the present invention was similar to that described in U.S. patent application Ser. No. 08/156,181, filed Nov. 22, 1993 (Singh, et al.), the relevant portions of which are incorporated herein by reference particularly as to the preparation of chemiluminescers and photosensitizers and of latex beads containing either a chemiluminescer or a photosensitizer and as to the manner of conducting an assay using such beads.

Figure 4:
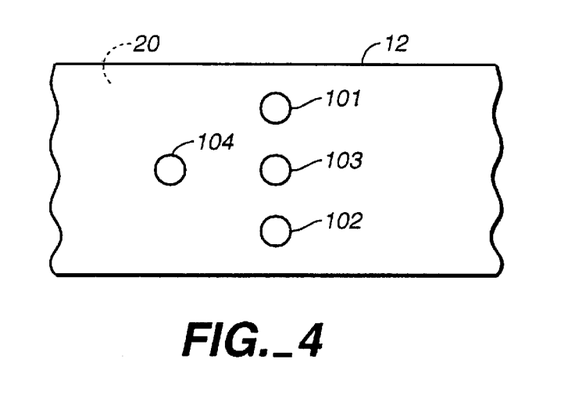
FIG. 4 is a depiction of drops created during an assay for digoxin using an embodiment of the present invention.

Referring to FIGS. 1, 2 and 4, two reagents were preloaded into a pair of receptacles in cassette 30, which was positioned on platform 33 such that pipette 22 accessed the reagents in those receptacles. Reagent A consisted of a buffer pH 8.2 (0.1M TRIS-HCl, 0.3M NaCl, 25 mM ethylenediaminetetraacetate (EDTA), 0.1% bovine serum albumin (BSA), 0.1% Dextran T-500 (R), 0.12% Kathon (R) (a preservative sold by Rohm and Haas) and 1/320 dilution of Heterophilic Blocking Reagent 1 (manufactured by Scantibodies Laboratory, Santee, Calif.) with 120 µ/g/ml of latex particles suspended in it. These particles contained a chemiluminescer (thioxene C-26 of Singh, et al., supra) and a europium chelate, namely, $Eu(TTA)_3$ of Singh, et al., supra, and had antibodies for digoxin bound to their surface by means of a biotin-streptavidin linkage. Reagent B consisted of a buffer (same as for Reagent A) with 24 µg/ml of latex particles suspended in it. These latter particles were prepared in a manner similar to that described by Singh, et al., supra, and contained the photosensitizer tetradecyl squarate (TDS) (prepared in a manner similar to that described in U.S. Pat. No. 4,830,786) and had digoxin molecules bound to their surface. The serum sample was contained in receptacle 28, also accessible to pipette 22.

The rigid support 20 and its cover 15 (see FIG. 2), as well as the reagents in cassette 30, were maintained at 32° C. The pipette tips 19 and 21 were filled with silicone oil from reservoir 27 of viscosity 50 centistokes. The tips were essentially polypropylene cylinders, with an inner diameter of 1 m, outer diameter of 2 mm, and length of 50 mm. The wall of the pipette tips was tapered down to an outer diameter of 1.5 mm over the last 4.5 mm Of its length. The pipette tip was prepared for fluid transfers by delivering one to two microliters of silicone oil to support 12, which was in the form of a tape. This step was only necessary at the beginning of an automated run. The silicone oil was drawn up the outside of the pipette tip by capillary forces to a height of at least 3 mm above the open end of the tip.

The sequence of operations in the assay was as follows: Pipette 22 was operated to draw 2 µl of air into its tip, which was then positioned 2 mm below the surface of the liquid in the cassette receptacle containing reagent A and 20 µl of that liquid is aspirated. The pipette tip was then withdrawn from the liquid and positioned over location 101 (see FIG. 4) on the support 12, in line with the reagent cassette 30 and sample receptacle 28. The pipette tip was lowered to a height 1.5 mm above support 12 and the liquid, air gap, and a small amount of silicone oil were deposited at location 101 on the surface of support 12. The total volume driven out of the pipette was 23 µl. The pipette then carried out the same sequence of steps to deposit a drop of reagent B at location 102. The support 12 was a film of transparent Mylar D, 0.005 inches thick and 1.96 inches wide.

The pipette drew in 2 µl of air and the pipette was then positioned such that its open end penetrated the drop at location 101 and was at a height of 0.5 mm above the support 12. The pipette drew in 15 µl of the liquid in the drop. The tip was withdrawn from the drop and 2 µl of air was aspirated. The pipette then was moved to the serum sample receptacle 28 and was immersed 2 mm below the liquid surface and 3 µl of serum was aspirated. The pipette was then moved to position 103 and was positioned 1.5 mm above the support surface and 23 µl volume was dispensed. The two liquid volumes were merged into one drop as they were deposited on the support, the air gaps were expelled, and 1 µl of excess silicone oil was dispensed over the drop. A mixing actuator was located just below and in contact with support 12 at position 103. The actuator was caused to oscillate approximately 0.01 inch vertically in a square wave pattern at 800 Hz. The oscillation was maintained for 6 seconds, so that the drop contents were thoroughly mixed by the oscillatory notion of the drop surface. The reaction between the serum digoxin and the reagent A particles began at this point.

The support was then advanced, as was the chain of samples, and a second reaction was prepared. When the first reaction mixture reached the location of pipette 24, the second part of the immunological reaction was initiated. In a sequence of steps similar to those initiating the first step, and using pipette 24 and only the liquids already present in drops on the support 12, 3 µl of the mixture of serum and reagent A (from location 103) and 15 µl of reagent B from the drop deposited initially at position 102 were placed at location 104 relative to the original three drops. A second mixing actuator mixed the drop so that the reaction between the reagent B particles and reagent A particles could begin.

As the support advanced on a precisely timed cycle, the mixture in location 104 reached read head 34. The signal reading process began with a solenoid actuating arm 37 and lowering over the drop a reflective enclosure 35, whose edges contacted the support in a substantially lightproof seal. Below the drop and the support were a hollow, reflective cylinder, an electromechanical shutter 41, and photomultiplier tube 40. The shutter was initially closed. At the top of the reflective enclosure was the end face of an optical fiber 43 that delivered light from a diode laser 42. The diode laser was switched on by computer control through an external modulated power supply (not shown in FIGS. 1, 2 or 4). The laser was switched on for one second. Ten milliseconds after the laser was switched off, the shutter was opened for one second, and light emitted from the reaction mixture was measured. Ten milliseconds after the shutter closed, the laser was again switched on and the process was repeated.

The total light measured over six cycles of illumination and detection constituted the signal for that sample. The signal was compared with that obtained using controls having predetermined amounts of digoxin. In this way the amount of digoxin in unknown samples was determined.

FIG. 4 shows the relative locations of the four drops 101–104 created in the analysis of each sample in one example of the use of the method. These locations are on movable support 12 and change position relative to the fixed support 20 as support 12 is advanced.

The above discussion includes certain theories as to mechanisms involved in the present invention. These theories should not be construed to limit the present invention in any way, since it has been demonstrated that the present invention achieves the results described.

The above description and examples disclose the invention including certain preferred embodiments thereof. Modifications of the methods described that are obvious to those of ordinary skill in the art such as molecular biology and related sciences are intended to be within the scope of the following claims and included within the metes and bounds of the invention.

What is claimed is:

1. An automatic analysis apparatus for analyzing a plurality of samples, said apparatus comprising:
   (a) a movable substantially inelastic and substantially planar surface,
   (b) a rigid support for said surface,
   (c) one or more liquid dispensing probes for dispensing a sample and reagents onto said surface to form droplets each containing a sample and reagents, said droplets being in containerless containment on said surface, said surface being substantially impervious to and non-reactive with said sample and reagents,
   (d) non-evaporative means for deforming said droplets without substantially stretching said surface thereby mixing said sample and said reagents contained in said droplets, said means being acoustic energy or electrostatic energy, and
   (e) an analyzer for analyzing said droplets, wherein said analyzer comprises:
   (f) a photodetector and
   (g) two reflective surfaces positioned with respect to said movable surface such that each of said droplets lies between said reflective surfaces, which substantially surround said droplet, at least one of said reflective surfaces having an opening for light emitted from said droplet to impinge on said photodetector.

2. A method for detecting light from a liquid medium subjected to photoactivation, said method comprising the steps of:
   (a) applying said liquid medium to a substantially planar and substantially inelastic transparent support, said liquid medium being in containerless containment thereon, said support being substantially impervious to and non-reactive with said liquid medium
   (b) positioning said support such that said liquid medium and said support are between two reflective surfaces that substantially surround said liquid medium, at least one of said surfaces having an opening for light emitted from said liquid medium to impinge on a photodetector comprising a photomultiplier tube having a shutter,
   (c) subjecting said liquid medium to photoactivation with said shutter closed, and
   (d) opening said shutter and detecting, by means of said photomultiplier tube, light emitted by said liquid medium.

3. The method of claim 2 wherein said photoemission is chemiluminescence.

4. The method of claim 2 wherein said medium is in the form of a drop on said transparent strip.

5. The method of claim 2 wherein said support is a strip.

6. A device for detecting light from a liquid medium subjected to photoactivation, said device comprising:
   (a) a transparent, substantially planar and substantially inelastic support that is impervious to and non-reactive with said liquid medium,
   (b) a photodetector comprising a photomultiplier tube having a shutter, and
   (c) two reflective surfaces positioned with respect to said support such that a medium applied to said support lies between said surfaces, which substantially surround said medium, at least one of said surfaces having an opening for light emitted from said medium to impinge on said photodetector, said medium being in containerless containment on said support.

7. The device of claim 6 wherein said support is a strip.

* * * * *